(12) United States Patent
Bartol et al.

(10) Patent No.: US 8,855,822 B2
(45) Date of Patent: *Oct. 7, 2014

(54) ROBOTIC SURGICAL SYSTEM WITH MECHANOMYOGRAPHY FEEDBACK

(75) Inventors: Stephen Bartol, Windsor (CA); Christopher Wybo, Royal Oak, MI (US)

(73) Assignee: Innovative Surgical Solutions, LLC, Wixom, MI (US)

( * ) Notice: Subject to any disclaimer, the term of this patent is extended or adjusted under 35 U.S.C. 154(b) by 351 days.

This patent is subject to a terminal disclaimer.

(21) Appl. No.: 13/428,693

(22) Filed: Mar. 23, 2012

(65) Prior Publication Data

US 2013/0253533 A1 Sep. 26, 2013

(51) Int. Cl.
G05B 15/00 (2006.01)
G05B 19/00 (2006.01)

(52) U.S. Cl.
USPC .......... 700/258; 700/245; 700/246; 700/247; 700/248; 700/251; 700/259; 700/260; 606/38; 600/554; 227/2

(58) Field of Classification Search
USPC ......... 700/245, 246, 247, 248, 251, 258, 259, 700/260; 318/566, 568.11, 568.12, 568.2, 318/568.21, 568.25; 227/2; 414/5; 600/545, 600/554; 606/38; 901/2, 9, 33, 34
See application file for complete search history.

(56) References Cited

U.S. PATENT DOCUMENTS

| | | | |
|---|---|---|---|
| 3,200,814 A | 8/1965 | Taylor et al. | |
| 3,565,080 A | 2/1971 | Ide et al. | |
| 3,797,010 A | 3/1974 | Adler et al. | |
| 4,817,628 A | 4/1989 | Zealear et al. | |
| 5,284,153 A | 2/1994 | Raymond et al. | |
| 5,284,154 A | 2/1994 | Raymond et al. | |

(Continued)

FOREIGN PATENT DOCUMENTS

| | | |
|---|---|---|
| EP | 1575010 A1 | 9/2005 |
| FR | 2920087 A1 | 2/2009 |
| WO | 0078209 A2 | 12/2000 |
| WO | 2007024147 A1 | 3/2007 |

OTHER PUBLICATIONS

Madeleine et al., Development of muscle fatigue as assessed by electromyography and mechanomyography during continuous and intermittent low-force contractions: effects of the feedback mode, Mar. 2002, European Journal of Applied Physiology, vol. 87, pp. 28-37.*

Alves-Kotzev, Natasha, Mechanomyography as an Access Pathway for Binary and Multifunction Control, 2010, University of Toronto, pp. 1-185.*

(Continued)

Primary Examiner — Khoi Tran
Assistant Examiner — Jaime Figueroa
(74) Attorney, Agent, or Firm — Quinn Law Group, PLLC.

(57) ABSTRACT

A robotic surgical system for performing a surgical procedure within the body of a subject includes an elongate surgical instrument, a robotic controller configured to control the motion of the distal end portion of the surgical instrument, and a mechanomyography feedback system in communication with the robotic controller. The mechanomyography feedback system includes a mechanical sensor configured to monitor a physical motion of a muscle and to provide a mechanomyography signal corresponding to the monitored physical motion. Additionally, the feedback system includes a processor configured to receive the mechanomyography signal, to determine if the received signal is indicative of an induced muscle response, and to provide a control signal to the robotic controller if an induced muscle response is detected.

20 Claims, 5 Drawing Sheets

(56) References Cited

U.S. PATENT DOCUMENTS

| | | | |
|---|---|---|---|
| 5,775,331 | A | 7/1998 | Raymond et al. |
| 6,324,432 | B1 | 11/2001 | Rigaux et al. |
| 6,361,508 | B1 | 3/2002 | Johnson et al. |
| 6,466,817 | B1 | 10/2002 | Kaula et al. |
| 6,500,128 | B2 | 12/2002 | Marino |
| 6,564,078 | B1 | 5/2003 | Marino et al. |
| 6,760,616 | B2 | 7/2004 | Hoey et al. |
| 6,807,438 | B1 | 10/2004 | Brun Del Re et al. |
| 6,972,199 | B2 | 12/2005 | Lebouitz et al. |
| 7,050,848 | B2 | 5/2006 | Hoey et al. |
| 7,079,883 | B2 | 7/2006 | Marino et al. |
| 7,177,677 | B2 | 2/2007 | Kaula et al. |
| 7,207,949 | B2 | 4/2007 | Miles et al. |
| 7,216,001 | B2 | 5/2007 | Hacker et al. |
| 7,236,832 | B2 * | 6/2007 | Hemmerling et al. .......... 607/48 |
| 7,470,236 | B1 | 12/2008 | Kelleher et al. |
| 7,522,953 | B2 | 4/2009 | Kaula et al. |
| 7,578,819 | B2 | 8/2009 | Bleich et al. |
| 7,582,058 | B1 | 9/2009 | Miles et al. |
| 7,657,308 | B2 | 2/2010 | Miles et al. |
| 7,664,544 | B2 | 2/2010 | Miles et al. |
| 7,668,588 | B2 | 2/2010 | Kovacs |
| 7,691,057 | B2 | 4/2010 | Miles et al. |
| 7,892,173 | B2 | 2/2011 | Miles et al. |
| 7,905,840 | B2 | 3/2011 | Pimenta et al. |
| 7,942,826 | B1 | 5/2011 | Scholl et al. |
| 7,959,577 | B2 | 6/2011 | Schmitz et al. |
| 7,962,191 | B2 | 6/2011 | Marino et al. |
| 7,981,058 | B2 | 7/2011 | Akay |
| 7,991,463 | B2 | 8/2011 | Kelleher et al. |
| 8,000,782 | B2 | 8/2011 | Gharib et al. |
| 8,016,776 | B2 | 9/2011 | Bourget et al. |
| 8,027,716 | B2 | 9/2011 | Gharib et al. |
| 8,055,349 | B2 | 11/2011 | Gharib et al. |
| 8,068,912 | B2 | 11/2011 | Kaula et al. |
| 8,075,499 | B2 | 12/2011 | Nathan et al. |
| 8,090,436 | B2 | 1/2012 | Hoey et al. |
| 8,133,173 | B2 * | 3/2012 | Miles et al. ................... 600/202 |
| 8,137,284 | B2 | 3/2012 | Miles et al. |
| 8,147,421 | B2 | 4/2012 | Farquhar et al. |
| 8,165,653 | B2 | 4/2012 | Marino et al. |
| 8,343,065 | B2 | 1/2013 | Bartol et al. |
| 8,343,079 | B2 * | 1/2013 | Bartol et al. ................... 600/595 |
| 2001/0031916 | A1 | 10/2001 | Bennett et al. |
| 2002/0038092 | A1 | 3/2002 | Stanaland et al. |
| 2002/0165590 | A1 | 11/2002 | Crowe et al. |
| 2003/0074037 | A1 | 4/2003 | Moore et al. |
| 2004/0077969 | A1 | 4/2004 | Onda et al. |
| 2004/0186535 | A1 | 9/2004 | Knowlton |
| 2004/0230138 | A1 * | 11/2004 | Inoue et al. ................... 600/595 |
| 2004/0243018 | A1 | 12/2004 | Organ et al. |
| 2005/0075578 | A1 | 4/2005 | Gharib et al. |
| 2005/0085741 | A1 | 4/2005 | Hoskonen et al. |
| 2005/0102007 | A1 | 5/2005 | Ayal et al. |
| 2005/0240086 | A1 | 10/2005 | Akay |
| 2005/0245839 | A1 | 11/2005 | Stivoric et al. |
| 2005/0280531 | A1 | 12/2005 | Fadem et al. |
| 2005/0283204 | A1 * | 12/2005 | Buhlmann et al. ............ 607/48 |
| 2006/0020177 | A1 | 1/2006 | Seo et al. |
| 2006/0052726 | A1 | 3/2006 | Weisz et al. |
| 2006/0135888 | A1 | 6/2006 | Mimnagh-Kelleher et al. |
| 2006/0270949 | A1 | 11/2006 | Mathie et al. |
| 2007/0038155 | A1 | 2/2007 | Kelly, Jr. et al. |
| 2007/0265671 | A1 | 11/2007 | Lund et al. |
| 2007/0276270 | A1 | 11/2007 | Tran |
| 2008/0051643 | A1 | 2/2008 | Park et al. |
| 2008/0058656 | A1 | 3/2008 | Costello et al. |
| 2008/0167695 | A1 | 7/2008 | Tehrani et al. |
| 2008/0234767 | A1 | 9/2008 | Salmon et al. |
| 2008/0287761 | A1 * | 11/2008 | Hayter et al. ................. 600/365 |
| 2008/0306363 | A1 * | 12/2008 | Chaiken et al. ............... 600/310 |
| 2008/0306397 | A1 | 12/2008 | Bonmassar et al. |
| 2008/0312560 | A1 | 12/2008 | Jamsen et al. |
| 2008/0312709 | A1 | 12/2008 | Volpe et al. |
| 2009/0036747 | A1 | 2/2009 | Hayter et al. |
| 2009/0062696 | A1 | 3/2009 | Nathan et al. |
| 2009/0069709 | A1 | 3/2009 | Schmitz et al. |
| 2009/0069722 | A1 | 3/2009 | Flaction et al. |
| 2009/0076336 | A1 * | 3/2009 | Mazar et al. .................. 600/300 |
| 2009/0171381 | A1 | 7/2009 | Schmitz et al. |
| 2009/0192416 | A1 | 7/2009 | Ernst et al. |
| 2009/0228068 | A1 | 9/2009 | Buhlmann et al. |
| 2009/0247910 | A1 | 10/2009 | Klapper |
| 2009/0306741 | A1 | 12/2009 | Hogle et al. |
| 2009/0318779 | A1 | 12/2009 | Tran |
| 2010/0137748 | A1 | 6/2010 | Sone et al. |
| 2010/0152619 | A1 | 6/2010 | Kalpaxis et al. |
| 2010/0152622 | A1 | 6/2010 | Teulings |
| 2010/0152623 | A1 | 6/2010 | Williams |
| 2010/0168559 | A1 | 7/2010 | Tegg et al. |
| 2010/0292617 | A1 * | 11/2010 | Lei et al. ...................... 600/595 |
| 2011/0004207 | A1 * | 1/2011 | Wallace et al. ................ 606/35 |
| 2011/0237974 | A1 | 9/2011 | Bartol et al. |
| 2012/0053491 | A1 | 3/2012 | Nathan et al. |
| 2013/0213659 | A1 | 5/2013 | Bartol et al. |
| 2014/0088612 | A1 * | 3/2014 | Bartol et al. .................. 606/130 |

OTHER PUBLICATIONS

Alves et al, The design and testing of a novel mechanomyogram-driven switch controlled by small eyebrow movements, 2010, Journal of Neuro Engineering and Rehabilitation 2010, 7:22, http://www.jneuroengrehab.com/content/7/1/22.*

Alves et al, The effect of accelerometer location on the classification of single-site forearm mechanomyograms, Jun. 2010, BioMedical Engineering OnLine 2010, 9:23, http://www.biomedical-engineering-online.com/content/9/1/23.*

Beck et al., Mechanomyographic amplitude and frequency responses during dynamic muscle actions: a comprehensive review, Dec. 2005, BioMedical Engineering OnLine 2005, 4:67 doi:10.1186/1475-925X-4-67.*

Ma, Martin, MMG sensor for muscle activity detection : low cost design, implementation and experimentation, Mar. 2009, Massey University, New Zeland, Masters of Engineering in Mechatronics, pp. 1-129.*

Bartol, Stephen MD, and Laschuk, Maria MD, "Arthroscopic Microscopic Discectomy in Awake Patients: The Effectiveness of Local/Neurolept Anaesthetic", Canadian Spine Society Meeting, Vernon, BC, Canada, Mar. 2002.

Bartol, Stephen MD, and Laschuk, Maria MD, "Use of Nerve Stimulator to Localize the Spinal Nerve Root During Arthroscopic Discectomy Procedures", Canadian Spine Society Meeting, Vernon, BC, Canada, Mar. 2002.

Begg et al. "Computational Intelligence for Movement Sciences: Neural Networks and Other Emerging Techniques" 2006.

Bourke et al. "A Threshold-Based Fall-Detection Algorithm Using a Bi-Axial Gyroscope Sensor" Medical Engineering and Physics 30 (2008) 84-90.

Fee Jr., James W.; Miller, Freeman; Lennon, Nancy; "EMG Reaction in Muscles About the Knee to Passive Velocity, Acceleration, and Jerk Manipulations"; Alfred I. duPont Hospital for Children, Gait Laboratory, 1600 Rockland Road, Wilmington, DE 19899, United States Journal of Electromyography and Kinesiology 19 (2009) 467-475.

Koceja, D.M., Bernacki, R.H. and Kamen, G., "Methodology for the Quantitative Assessment of Human Crossed-Spinal Reflex Pathways," Medical & Biological Engineering & Computing, Nov. 1991, pp. 603-606, No. 6, US.

Tarata, M.; Spaepen, A.; Puers, R.; "The Accelerometer MMG Measurement Approach, in Monitoring the Muscular Fatigue"; Measurement Science Review; 2001; vol. 1, No. 1.

Murphy, Chris; Campbell, Niall; Caulfield, Brian; Ward, Tomas and Deegan, Catherine; "Micro Electro Mechanical Systems Based Sensor for Mechanomyography", 19th international conference BIOSIGNAL 2008, Brno, Czech Republic.

Nijsen, Tamara M.E.; Aarts, Ronald M.; Arends, Johan B.A.M.; Cluitmans, Pierre J.M.; "Model for Arm Movements During Myoclonic Seizures"; Proceedings of the 29th Annual International Conference of the IEEE EMBS Cite Internationale, Lyon, France Aug. 23-26, 2007.

Ohta, Yoichi; Shima, Norihiro; Yabe, Kyonosuke; "Superimposed Mechanomyographic Response at Different Contraction Intensity in Medial Gastrocnemius and Soleus Muscles"; International Journal of Sport and Health Science, vol. 5, 63-70, 2007.

* cited by examiner

ROBOTIC SURGICAL SYSTEM WITH MECHANOMYOGRAPHY FEEDBACK

TECHNICAL FIELD

The present invention relates generally to minimally invasive robotic surgical systems.

BACKGROUND

Robotic surgery involves the use of one or more robotically manipulated surgical instruments, extending within a patient to perform a surgical procedure. Each surgical instrument may include a specially configured end effector disposed on a distal end portion of the instrument to effectuate, for example, a grasping routine. Robotic surgical systems enable minimally invasive surgical procedures to be performed with less trauma to the subject than in traditional surgical procedures, and may potentially have a greater degree of precision.

During a robotically assisted surgical procedure, a surgeon generally oversees the operation of the robotic manipulator in a tele-opritive manner while seated at a master station. The master station may include both a specially configured user input controls and a display. Display feedback provided to the surgeon may typically include direct visual feedback, such as from a robotically controlled endoscopic camera that may extend within the patient. From this visual feedback, the surgeon may direct the robotic manipulator to perform the desired task/procedure.

SUMMARY

A robotic surgical system for performing a surgical procedure within the body of a subject includes an elongate surgical instrument, a robotic controller configured to control the motion of the distal end portion of the surgical instrument, and a mechanomyography feedback system in communication with the robotic controller. The mechanomyography feedback system includes a mechanical sensor configured to monitor a physical motion of a muscle and to provide a mechanomyography signal corresponding to the monitored physical motion. Additionally, the feedback system includes a processor configured to receive the mechanomyography signal, to determine if the received signal is indicative of an induced muscle response, and to provide a control signal to the robotic controller if an induced muscle response is detected.

In one configuration, the robotic controller may be configured to prevent motion of the distal end portion of the surgical instrument in response to the control signal. In another configuration, the robotic controller may be configured to limit the range of motion of the elongate surgical instrument in response to the received control signal. When the surgical instrument includes an end effector actuatable in at least one degree of freedom, the robotic controller may be configured to prevent actuation of the end effector in response to the control signal.

The control signal may include an indication of a proximity between the distal end of the elongate surgical instrument and a nerve. In response to the detected proximity, the robotic controller may be configured to vary the speed of the distal end of the elongate surgical instrument.

An induced muscle response may be determined by computing a time derivative of acceleration from the received mechanomyography signal, and comparing the computed time derivative of acceleration from the mechanomyography signal to a jerk threshold. In an embodiment where the surgical instrument includes a stimulator configured to provide an electrical stimulus, an induced muscle response may include physical motion of the muscle attributable to a depolarization of a nerve innervating the muscle, wherein the depolarization of the nerve is induced by the provided electrical stimulus.

The robotic surgical system may further include a master station in communication with the robotic controller. The master station may be configured to receive an input from a user corresponding to an intended movement of the distal end of the surgical instrument and to provide a motion command to the robotic controller corresponding to the received input. Additionally, the master station may be configured to provide at least one of a visual alert and auditory alert if an induced muscle response is detected.

A method of nerve avoidance during robotically assisted surgery may include: controlling the motion of a distal end portion of an elongate surgical instrument using a robotic controller; receiving a mechanomyography signal from at least one mechanical sensor; determining if the received mechanomyography signal is indicative of an induced muscle response; and providing a control signal to the robotic controller if an induced muscle response is detected.

The method may further include electronically limiting the range of motion of the distal end portion of the elongate surgical instrument in response to the received control signal. Alternatively, it may include preventing motion of the distal end portion of the surgical instrument in response to the control signal. Where the control signal includes an indication of proximity between the distal end portion and a nerve, the method may include varying the speed of the distal end of the elongate surgical instrument as a function of the indicated proximity.

The above features and advantages and other features and advantages of the present invention are readily apparent from the following detailed description of the best modes for carrying out the invention when taken in connection with the accompanying drawings.

DETAILED DESCRIPTION

Figure 1:
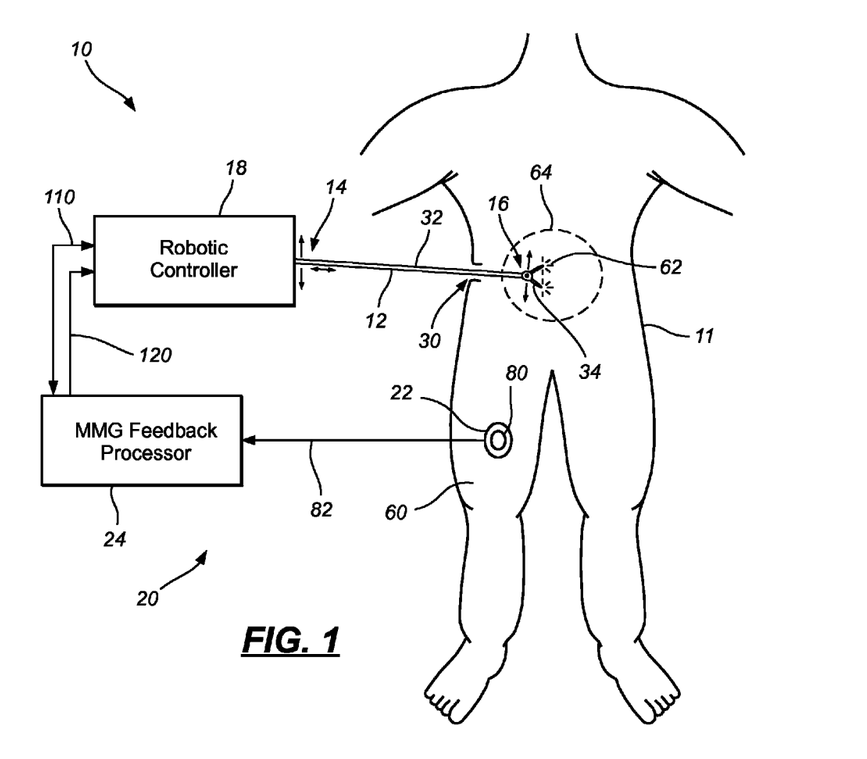
FIG. 1 is a schematic illustration of a robotic surgical system with mechanomyographic feedback being used in conjunction with a human subject.

Referring to the drawings, wherein like reference numerals are used to identify like or identical components in the various views, FIG. 1 schematically illustrates a robotic surgical system 10 for performing a surgical procedure within the body of a human subject 11. As illustrated, the robotic surgical system 10 includes an elongate surgical instrument 12 having a proximal end portion 14 and a distal end portion 16, a robotic controller 18 configured to control the motion of the distal end portion 16 of the surgical instrument 12, and a mechanomyography (MMG) feedback system 20 in communication with the robotic controller 18. The MMG feedback system 20 may include at least one mechanical sensor 22 and an MMG feedback processor 24 in communication with the mechanical sensor 22.

During a surgical procedure, the surgical instrument 12 may extend through an opening 30 in the body of the subject 11, with the distal end portion 16 disposed within the body of the subject 11, and the proximal end portion 14 disposed outside of the body of the subject 11. In one configuration, the surgical instrument 12 may generally be defined by a rigid elongate body 32, such that movement of the proximal end portion 14 of the instrument 12 may result in a predictable movement of the distal end portion 16 of the instrument 12.

The surgical instrument 12 may further include an end effector 34 disposed at the distal end portion 16. The end effector 34 may be responsible for performing one or more cutting, grasping, cauterizing, or ablating functions, and may be selectively actuatable in at least one degree of freedom (i.e. a movable degree of freedom, such as rotation, or an electrical degree of freedom, such as selectively delivering ablative energy). Additionally, the end effector 34 may be configured to selectively rotate and/or articulate about the distal end portion 16 of the surgical instrument 12 to enable a greater range of motion/dexterity during a procedure.

In one embodiment, such as generally illustrated in FIG. 1, the end effector 34 may be configured to resemble forceps, and may have one or more controllably movable jaws adapted to articulate about a hinged joint. The selective articulation of the one or more jaws may be enabled, for example, by cables or pull wires extending to the robotic controller through the rigid elongate body 32 of the instrument 12.

Figure 2:
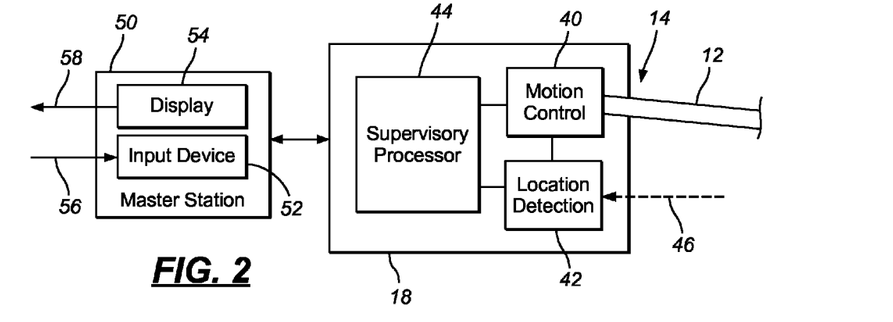
FIG. 2 is a schematic diagram of a robotic controller.

The robotic controller 18 may be responsible for controllably performing a minimally invasive surgical procedure within the body of the subject 11 by controllably manipulating the proximal end 14 of the surgical instrument 12 in a manner that results in a controlled motion of the distal end portion 16. As generally illustrated in FIG. 2, in one configuration, the robotic controller 18 may include a motion controller 40, a location detection module 42 and a supervisory processor 44. The motion controller 40 may include a plurality of motors, linear actuators, or other such components that may be required to manipulate the proximal end 14 of the surgical instrument 12 in six or more degrees of freedom. (e.g., three degrees of translation, three degrees of rotation, and/or one or more degrees of actuation). Additionally, the motion controller 40 may include one or more processors or digital computers and/or power electronics that may be required to convert a received motion command into a physical actuation of a motor or actuator.

The location detection module 42 may include one or more digital computers or processing devices that may be configured to determine the position/motion of the distal end portion 16 of the surgical instrument 12, such as relative to one or more external reference frames. In one configuration, the location detection module 42 may monitor the behavior of the motion controller 40 to determine the motion of the distal end portion 16 using kinematic relationships of the surgical instrument 12. In another configuration, the location detection module 42 may receive a location signal 46 from an external, positioning system (not shown), which may resolve the position of the distal end portion 16 of the surgical instrument 12 using, for example, ultrasound energy, magnetic energy, or electromagnetic energy that may be propagated through the subject 11.

The supervisory processor 44 may be embodied as one or more digital computers or data processing devices, each having one or more microprocessors or central processing units (CPU), read only memory (ROM), random access memory (RAM), electrically-erasable programmable read only memory (EEPROM), a high-speed clock, analog-to-digital (A/D) circuitry, digital-to-analog (D/A) circuitry, input/output (I/O) circuitry, power electronics/transformers, and/or signal conditioning and buffering electronics. The individual control routines/systems resident in the supervisory processor 44 or readily accessible thereby may be stored in ROM or other suitable tangible memory location and/or memory device, and automatically executed by associated hardware components of the processor 44 to provide the respective control functionality. In one embodiment, the supervisory processor 44 may provide the motion controller 40 with actuation commands in a closed loop manner using the positional feedback provided by the location detection module 42. The supervisory processor 44 may perform any combination of feedforward, feedback, and/or predictive control schemes to accurately control the motion and/or actuation of the distal end portion 16 of the surgical instrument 12.

Additionally, the robotic controller 18 may be in communication with a master station 50 that includes a user input device 52 and a user feedback device such as a display 54. The user input device 52 may receive an input 56 from a user that corresponds to an intended movement of the distal end portion 16 of the surgical instrument 12. The master station 50 may then provide a motion command to the robotic controller 18 that corresponds to the received input 56. Similarly, the master station 50 may receive visual information 58 from the robotic controller and convey it to the user via the display 54.

While FIG. 2 provides one embodiment of a robotic controller 18, other embodiments, configurations, and or control schemes may similarly be used to manipulate the surgical instrument 12 in a manner that results in a controlled, and intended motion of the distal end portion 16. While the robotic controller 18 and surgical instrument 12 described above are generally of the kind used for robotic laparoscopy, such description is made for illustrative purposes and should not be limiting. Other minimally invasive surgical systems that employ a robotic controller 18 to control the motion of the distal end of an elongate surgical instrument may include, for example, robotic catheter systems and/or robotic endoscopic systems.

Referring again to FIG. 1, the robotic surgical system 10 includes a MMG feedback system 20 in communication with the robotic controller 18. As described above, the MMG feedback system 20 may include at least one mechanical sensor 22 and an MMG feedback processor 24 in communication with the mechanical sensor 22. The MMG feedback system 20 may provide the robotic controller 18 with an awareness of nerves that may be adjacent to the distal end portion 16 of the surgical instrument 12. In this manner, the robotic system 10 may avoid manipulating tissue (either through translational motion or actuation of an end effector 34) that may jeopardize neural integrity.

As generally illustrated in FIG. 1, the mechanical sensor 22 may be configured to be placed in mechanical communication with one or more muscles 60 of the subject 11 such that it may be capable of monitoring the physical motion of the one or more adjacent muscles 60.

Figure 3:
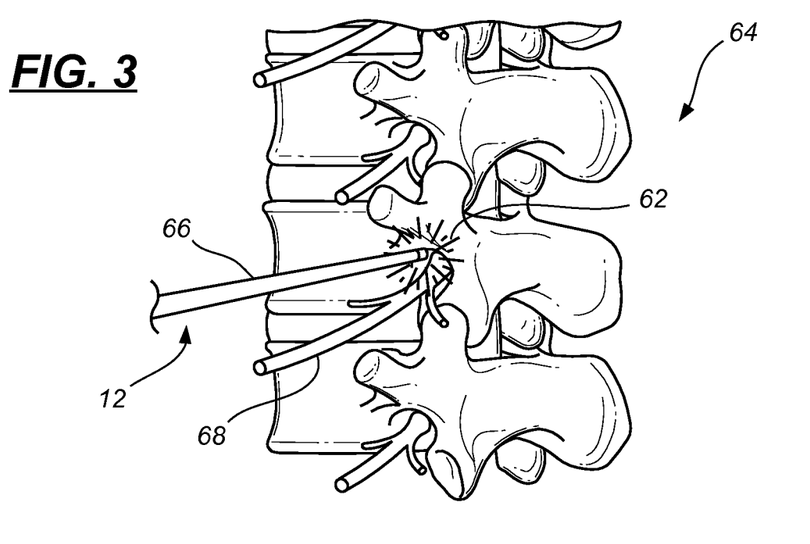
FIG. 3 is a schematic side view of a treatment area including a lumbar spine.

During a surgical procedure, the elongate surgical instrument 12 may emit a stimulus 62 within a treatment region 64 of the subject 11, where one or more nerves are expected to exist. The stimulus 62 may be, for example, an electrical stimulus, though may alternatively be a thermal, chemical, ultrasonic, or infrared stimulus. Referring to FIG. 3, which represents the elongate surgical instrument 12 as an electrocautery probe 66, if the stimulus 62 is provided at, or sufficiently close to a nerve within the treatment region 64 (e.g., nerve 68), the stimulus 62 may be received by the nerve 68 in a manner that causes the nerve to depolarize. A depolarizing nerve may then induce a response in a muscle that is innervated by the nerve, which may then be detected by the mechanical sensor 22. Examples of expected muscle responses may include, for example, physical motion, acceleration, displacement, or vibration of the muscle.

Figure 4:
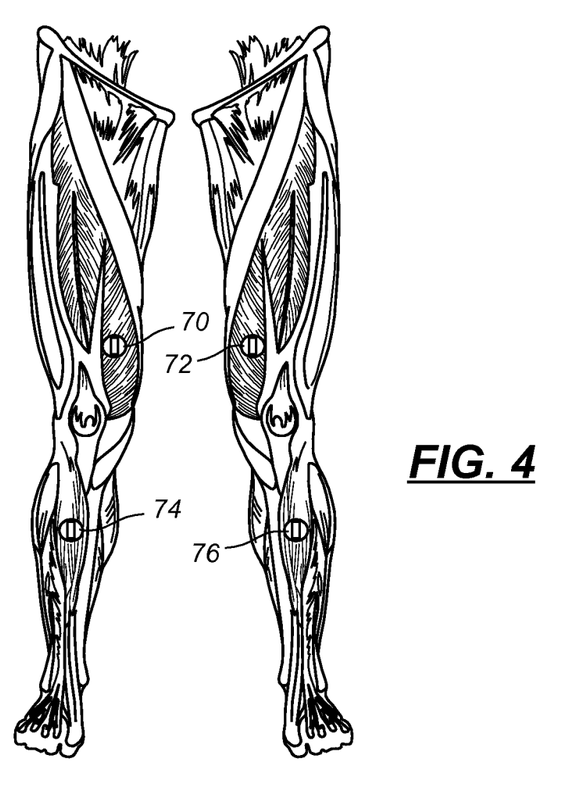
FIG. 4 is a schematic illustration of a plurality of mechanical sensors in mechanical communication with various muscles of a subject.

By way of example, and not limitation, during a discectomy of the lumbar spine, a surgeon may know that the nerves exiting the L2, L3 and L4 foramen are potentially located in the treatment region 64. As illustrated in FIG. 4, the surgeon may place a mechanical sensor 22 on each muscle innervated by those nerves. For instance, sensor devices 70, 72 may be placed on the vastus medialis muscles, which are innervated by nerves exiting the L2 and L3 foramen. Likewise sensors 74, 76 may be placed on the tibialis anterior muscles, which are innervated by the nerves exiting the L4 foramen.

Referring again to FIG. 1, in one configuration, the mechanical sensor 22 may include an accelerometer 80 configured to monitor the mechanical motion of the adjacent muscle and to generate a corresponding mechanomyography (MMG) signal 82 in response. The MMG feedback processor 24 may receive the MMG signal 82 through a wired or wireless communication link and may attempt to determine if the received MMG signal 82 is indicative of a muscle response induced by the provided stimulus 62. To discern whether a sensed motion is an induced muscle response or an inadvertent movement of the muscle (e.g., an external bump), the MMG feedback processor 24 may examine various characteristics of the MMG signal 82, such as peak magnitude and jerk (i.e., the time derivative of acceleration).

Figure 5:
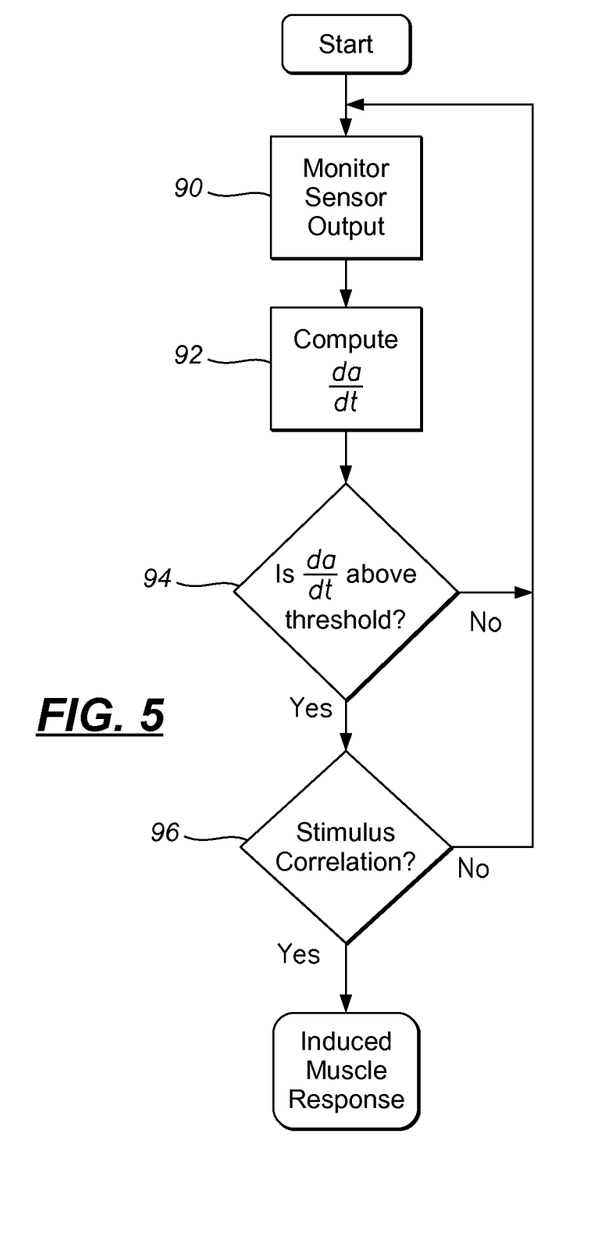
FIG. 5 is a flow diagram illustrating a method of detecting an induced muscle response.

As illustrated in FIG. 5, to detect an induced muscle response, the MMG feedback processor 24 may first receive and register the raw readings of the accelerometer 80 in step 90 (e.g., via MMG signal 82). The MMG feedback processor 24 may then use these raw readings to compute or derive the amount of muscle "jerk" experienced by the sensor in step 92 (i.e., "jerk," or a "jerk value," is the rate of change of the sensed acceleration (i.e. da/dt)). While a jerk value may be derived by taking the time derivative of acceleration, it may also be computed from other sensed mechanical parameters, such as velocity or position. It has been found that a muscle response induced by a provided stimulus 62 may correspond to a particular jerk rate. By setting an appropriate threshold and comparing the derived jerk to the threshold (step 94), the system may be able to initially filter recorded readings to discriminate between a stimulator induced response, a patient-intended muscle movement, and an unintended environmental response (e.g. bumping the patient table).

Figure 6:
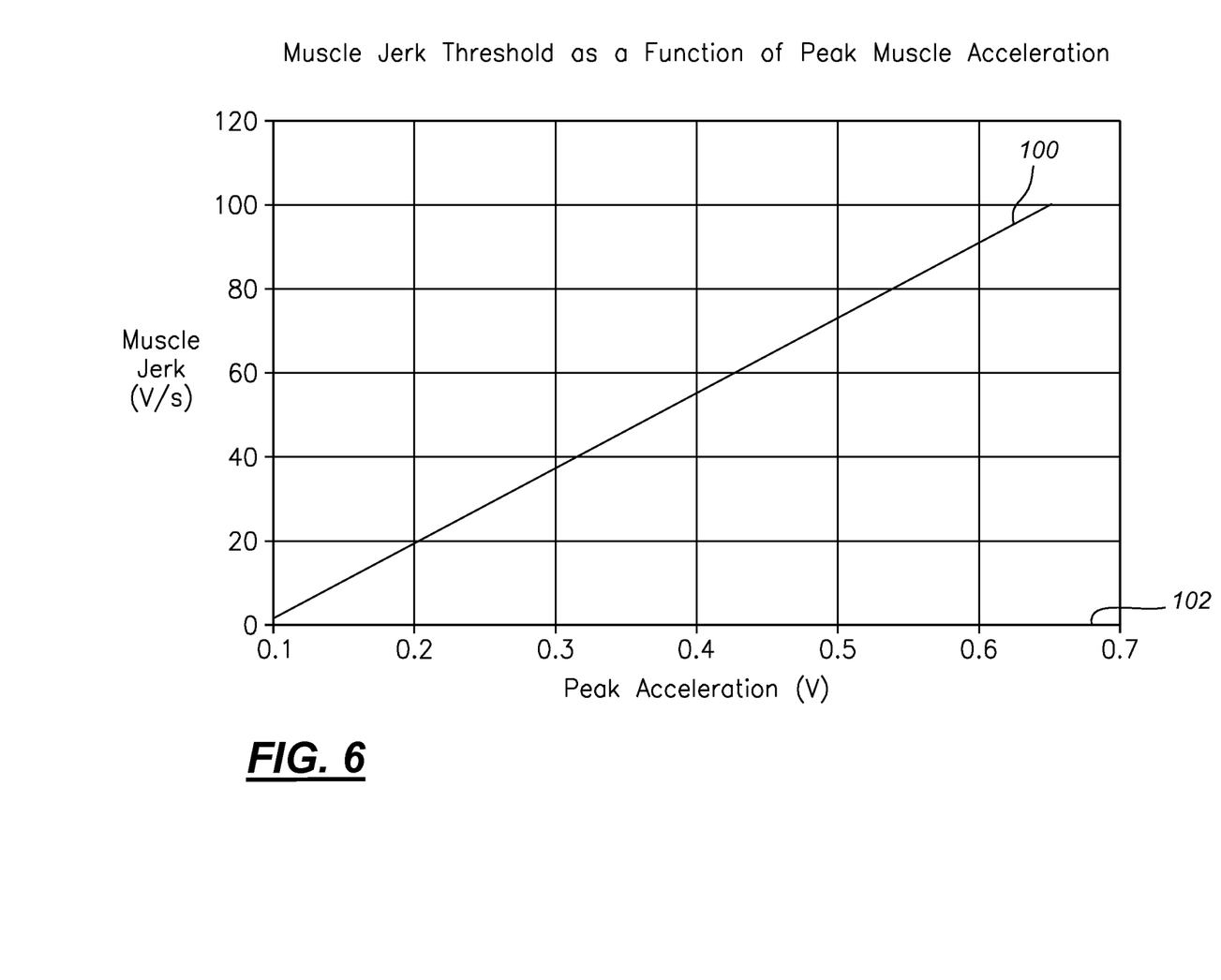
FIG. 6 is a graph illustrating a muscle jerk threshold as a function of peak muscle acceleration.

The jerk threshold used in step 94 for detecting an event may be varied based on the type or timing of the detected sensor response. For example, in an embodiment, as generally shown in FIG. 6, the jerk threshold 100 may be an increasing function of sensed accelerometer peak amplitude 102. In other embodiments, it may be a constant threshold.

In an embodiment where the surgical instrument 12 provides an electrical stimulus 62, the MMG feedback processor 24 may further detect whether the electrical stimulus 62 was transmitted immediately prior to a sensed response/muscle jerk (e.g., in step 96). For example, in one configuration, the robotic controller 18 may initiate the transmission of the electrical stimulus 62 and may provide the MMG feedback processor 24 with an indication of the transmission and the magnitude of the stimulus 62 (i.e., via data connection 110). In another configuration, the stimulus 62 may be provided to the robotic controller 18 and/or surgical instrument 12 by the MMG feedback processor 24 (i.e. via data connection 110). By correlating the MMG signal 82 with the known timing and/or magnitude of the stimulus 62, the system may further filter out non-induced muscle responses. In other embodiments, other sensed or derived parameters may be used for the purpose of identifying stimulator-induced muscle response, as well as for testing the magnitude of the induced response.

Figure 7:
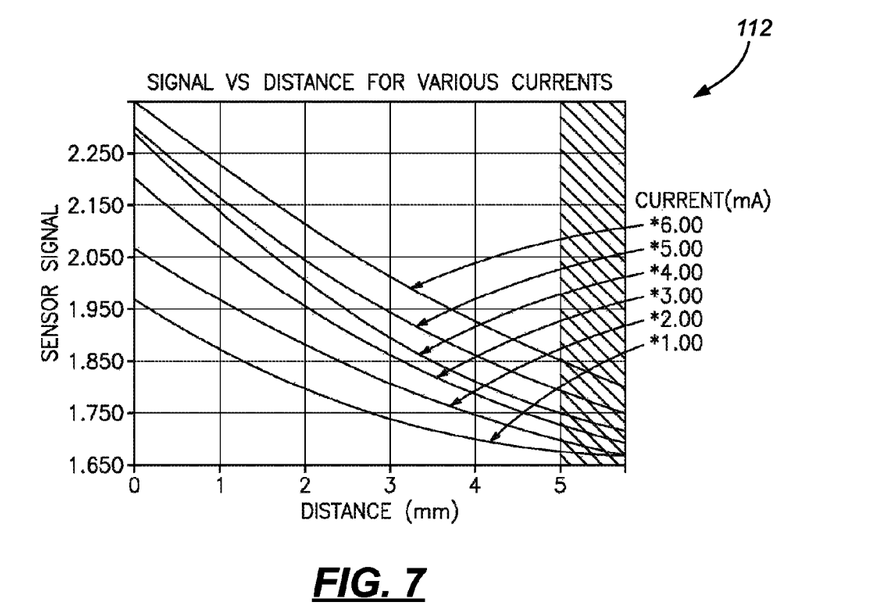
FIG. 7 is a plot of distance between a stimulator and a depolarized nerve as a function of both the magnitude of a received mechanomyography signal and the magnitude of a provided stimulus.

Following the detection of an induced muscle response, the MMG feedback processor 24 may further determine a distance or proximity of the depolarized nerve from the distal end portion 16 of the surgical instrument 12. This determination may be accomplished by comparing the magnitude of the received MMG signal 82 with the magnitude of the provided stimulus, as generally illustrated in FIG. 7. In one configuration, the MMG feedback processor 24 may maintain one or more such reference charts (such as chart 112 illustrated in FIG. 7) in an associated memory, such as in the form of a look-up table.

Referring again to FIG. 1, if the MMG feedback processor 24 detects an induced muscle response via the mechanical sensor 22, it may then provide a control signal 120 to the robotic controller 18. The control signal 120 may include an indication that an induced muscle response was detected, and may further include an indication of proximity between the distal end portion 16 of the surgical instrument 12 and a depolarized nerve.

Upon receipt of a control signal 120, the robotic controller 18 may artificially constrain the motion of the distal end portion 16 of the surgical instrument 12 to avoid inadvertent contact with a proximate nerve. For example, in one configuration, the robotic controller 18 may be configured to prevent all motion of the distal end portion 16 of the surgical instrument 12 in response to the received control signal 120. As such, if the distal end portion 16 was in motion, the received control signal 120 may cause the controller 18 to halt such motion and await a further command from the user. Additionally, the robotic controller 18 may be configured to limit or prevent actuation of an end effector 34 upon receipt of the control signal 120. Conversely, in certain therapeutic procedures, the robotic controller 18 may be configured to actuate the end effector 34 upon receipt of the control signal 120 (e.g., selectively deliver ablative energy to tissue proximate to the nerve).

Figure 8:
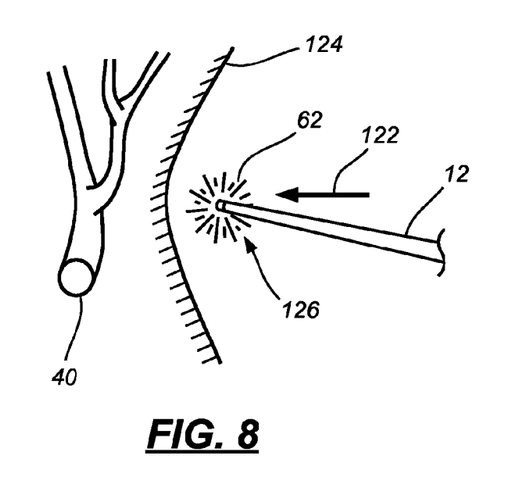
FIG. 8 is a schematic cross-sectional view of a distal end portion of an elongate surgical instrument moving with respect to a nerve of a subject.

In another configuration, such as schematically illustrated in FIG. 8, upon receipt of the control signal 120, the robotic controller may note the direction 122 of current motion of the surgical instrument 12, and may limit further instrument motion in that direction 122 (or directions with a component vector substantially aligned with the direction 122 of motion).

Figure 9:
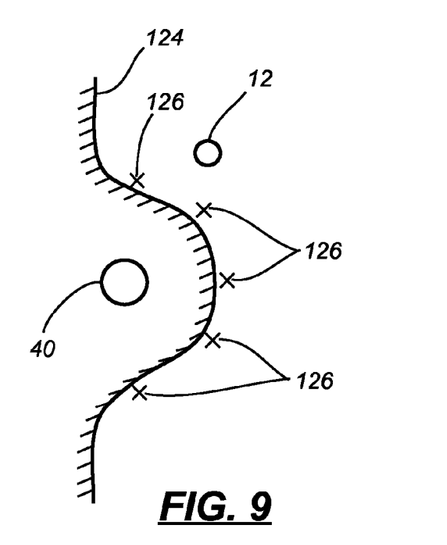
FIG. 9 is a schematic cross-sectional view of FIG. 8, with a virtual barrier being erected about the nerve.

In still another configuration, the robotic controller 18 may construct a virtual barrier 124 based on the direction of motion of the surgical instrument 12, and the location 126 of the instrument 12 when the control signal 120 was received. The virtual barrier 124 may be maintained in an associated memory of the robotic controller 18, and may limit the allowed range of motion of the surgical instrument 12, such that the surgical instrument 12 is artificially restricted from crossing the virtual barrier 124. As generally illustrated in FIG. 9, as the surgical instrument 12 moves, the virtual barrier 124 may be refined according to the receipt of successive control signals 120/locations 126.

Once a nerve is detected, the robotic controller 18 may be configured to vary the permitted speed of the distal end portion 16 of the surgical instrument 12 as a function of the indicated proximity between the real-time location of the instrument 12 and the estimated position of the nerve. As such, the instrument 12 may be allowed to move more quickly and/or at a higher rate of speed when it is farther from the nerve. In this manner, the precision of the movements may be enhanced as one or more nerves become more proximate.

If the presence of a proximate nerve is detected (via an induced muscle response), and/or if an action is performed by the robotic controller 18 to adjust or limit the allowed motion of the surgical instrument 12, the robotic controller 18 may likewise transmit an alert (i.e., a visual alert or an auditory alert) to the user via the master station 50.

Using the system described above, robotic, minimally invasive surgery may be performed in a manner that may allow a surgeon to be aware of nerves/nerve roots that may lie within the treatment area. This is important because neural tissue may often be visually indistinguishable from surrounding tissue, thus traditional visual methods of guidance and control may be ineffective. In this manner, using the above-described system, care may be taken to avoid manipulating neural tissue (either intentionally or inadvertently) in a manner that may injure one or more nerves and/or result in long-term paralysis. Said another way, the described system may allow the user and/or robotic controller to "see" the nerves within the treatment area using a non-visual and/or indirect sensing means. Once their presence is identified, appropriate care may be taken to avoid inadvertent or unintended contact with them.

While the best modes for carrying out the invention have been described in detail, those familiar with the art to which this invention relates will recognize various alternative designs and embodiments for practicing the invention within the scope of the appended claims. It is intended that all matter contained in the above description or shown in the accompanying drawings shall be interpreted as illustrative only and not as limiting.

The invention claimed is:

1. A robotic surgical system for performing a surgical procedure within the body of a subject, the robotic surgical system comprising:
   an elongate surgical instrument having a proximal end portion and a distal end portion;
   a robotic controller configured to control the motion of the distal end portion of the surgical instrument; and
   a mechanomyography feedback system in communication with the robotic controller, the mechanomyography feedback system including:
      a mechanical sensor configured to:
         monitor a physical motion of a muscle; and
         provide a mechanomyography signal corresponding to the monitored physical motion; and
      a processor configured to:
         receive the mechanomyography signal;
         determine if the received mechanomyography signal is indicative of an induced muscle response; and
         provide a control signal to the robotic controller if an induced muscle response is detected.

2. The robotic surgical system of claim 1, wherein the robotic controller is configured to limit the range of motion of the elongate surgical instrument in response to the received control signal.

3. The robotic surgical system of claim 1, wherein the robotic controller is configured to prevent motion of the distal end portion of the surgical instrument in response to the control signal.

4. The robotic surgical system of claim 1, wherein the control signal is indicative of a proximity between the distal end portion of the elongate surgical instrument and a nerve.

5. The robotic surgical system of claim 4, wherein the robotic controller is configured to vary the speed of the distal end of the elongate surgical instrument as a function of the indicated proximity.

6. The robotic surgical system of claim 1, wherein the processor of the mechanomyography feedback system is configured to determine if the received mechanomyography signal is indicative of an induced muscle response by:
   computing a time derivative of acceleration from the received mechanomyography signal; and
   comparing the computed time derivative of acceleration from the mechanomyography signal to a jerk threshold.

7. The robotic surgical system of claim 1, wherein the distal end portion of the surgical instrument includes a stimulator configured to provide an electrical stimulus.

8. The robotic surgical system of claim 7, wherein an induced muscle response includes physical motion of the muscle attributable to a depolarization of a nerve innervating the muscle; and
   wherein the depolarization of the nerve is induced by the provided electrical stimulus.

9. The robotic surgical system of claim 1, wherein the elongate surgical instrument includes an end effector disposed at the distal end portion, the end effector being actuatable in at least one degree of freedom;
   wherein the robotic controller is configured to control the actuation of the end effector; and
   wherein the robotic controller is configured to prevent actuation of the end effector in response to the control signal.

10. The robotic surgical system of claim 1, wherein the elongate surgical instrument includes an end effector disposed at the distal end portion, the end effector being actuatable in at least one degree of freedom;
    wherein the robotic controller is configured to control the actuation of the end effector; and
    wherein the robotic controller is configured to actuate the end effector in response to the control signal.

11. The robotic surgical system of claim 1, further comprising a master station in communication with the robotic controller and configured to:
    receive an input from a user corresponding to an intended movement of the distal end portion of the surgical instrument; and
    provide a motion command to the robotic controller corresponding to the received input; and
    wherein the master station is configured to provide at least one of a visual alert and auditory alert if an induced muscle response is detected.

12. A method of nerve avoidance during robotically assisted surgery comprising:
    controlling the motion of a distal end portion of an elongate surgical instrument using a robotic controller;
    receiving a mechanomyography signal from at least one mechanical sensor;
    determining if the received mechanomyography signal is indicative of an induced muscle response; and
    providing a control signal to the robotic controller if an induced muscle response is detected.

13. The method of claim 11, further comprising electronically limiting the range of motion of the distal end portion of the elongate surgical instrument in response to the received control signal.

14. The method of claim 11, further comprising preventing, via the robotic controller, motion of the distal end portion of the surgical instrument in response to the control signal.

15. The method of claim 11, wherein the control signal is indicative of a proximity between the distal end portion of the elongate surgical instrument and a nerve.

16. The method of claim 14, further comprising varying the speed of the distal end portion of the elongate surgical instrument as a function of the indicated proximity.

17. The method of claim 11, wherein determining if the received mechanomyography signal is indicative of an induced muscle response includes:
   computing a time derivative of acceleration from the received mechanomyography signal; and
   comparing the computed time derivative of acceleration from the mechanomyography signal to a jerk threshold.

18. The method of claim 11, providing an electrical stimulus via a stimulator associated with the distal end portion of the elongate surgical instrument.

19. The method of claim 11, further comprising providing at least one of a visual alert and an auditory alert to a user if an induced muscle response is detected.

20. The method of claim 11, further comprising:
   monitoring a physical motion of a muscle of a subject using the at least one mechanical sensor; and
   generating the mechanomyography signal via the at least one mechanical sensor, wherein the mechanomyography signal corresponds to the monitored physical motion.

* * * * *

UNITED STATES PATENT AND TRADEMARK OFFICE
CERTIFICATE OF CORRECTION

PATENT NO. : 8,855,822 B2
APPLICATION NO. : 13/428693
DATED : October 7, 2014
INVENTOR(S) : Stephen Bartol et al.

It is certified that error appears in the above-identified patent and that said Letters Patent is hereby corrected as shown below:

In The Claims

Column 7, claim 1, line 7:
Beginning after "distal end portion of the surgical instrument" insert the text: --within the body of the subject-- so that the line should read: "distal end portion of the surgical instrument within the body of the subject; and"

Column 7, claim 1, line 18:
Beginning after "is indicative of an induced muscle response" insert the text: --that is attributable to the elongate surgical instrument-- so that the line should read: "is indicative of an induced muscle response that is attributable to the elongate surgical instrument; and"

Column 8, claim 12, line 61:
Beginning after "surgical instrument using a robotic controller" insert the text: --, the elongate surgical instrument being configured to provide a stimulus from the distal end portion-- so that the line should read: "surgical instrument using a robotic controller, the elongate surgical instrument being configured to provide a stimulus from the distal end portion;"

Column 8, claim 12, line 65:
Beginning after "indicative of an induced muscle response" insert the text: --that is attributable to the stimulus provided by the elongate surgical instrument-- so that the line should read: "indicative of an induced muscle response that is attributable to the stimulus provided by the elongate surgical instrument; and"

Column 9, claim 13, line 1:
"13. The method of claim 11" should read: --13. The method of claim 12--

Column 9, claim 14, line 5:
"14. The method of claim 11" should read: --14. The method of claim 12--

Signed and Sealed this
Twenty-first Day of July, 2015

Michelle K. Lee
*Director of the United States Patent and Trademark Office*

CERTIFICATE OF CORRECTION (continued)
U.S. Pat. No. 8,855,822 B2

Column 9, claim 15, line 8:
"15. The method of claim 11" should read: --15. The method of claim 12--

Column 9, claim 16, line 11:
"16. The method of claim 14" should read: --16. The method of claim 15--

Column 9, claim 17, line 14:
"17. The method of claim 11" should read: --17. The method of claim 12--

Column 10, claim 18, line 3:
Beginning after "18. The method of claim" remove "claim 11" and insert: --claim 12, wherein the stimulus is an electrical stimulus;--
Beginning after "wherein the stimulus is an electrical stimulus;", the word "an" should be removed and the line should read: --the method further comprising providing the electrical stimulus via a stimulator associated with the distal end portion of the elongate surgical instrument-- so that the lines should read: "18. The method of claim 12, wherein the stimulus is an electrical stimulus;
the method further comprising providing the electrical stimulus via a stimulator associated with the distal end portion of the elongate surgical instrument"

Column 10, claim 19, line 6:
"19. The method of claim 11" should read: --19. The method of claim 12--

Column 10, claim 20, line 9:
"20. The method of claim 11" should read: --20. The method of claim 12--